United States Patent [19]

Bolton et al.

[11] Patent Number: 4,975,376
[45] Date of Patent: Dec. 4, 1990

[54] CLASS II RESTRICTION ENDONUCLEASE KSPI AND A PROCESS FOR OBTAINING IT

[75] Inventors: Bryan J. Bolton, Shirley, England; Michael Jarsch, Bad Heilbrunn, Fed. Rep. of Germany; Gudrun Schmitz, Bernried, Fed. Rep. of Germany; Christoph Kessler, Munich, Fed. Rep. of Germany

[73] Assignee: Boehringer Mannheim GmbH, Mannheim, Fed. Rep. of Germany

[21] Appl. No.: 331,670

[22] Filed: Mar. 30, 1989

[30] Foreign Application Priority Data

Apr. 2, 1988 [DE] Fed. Rep. of Germany ....... 3811278

[51] Int. Cl.$^5$ .................. C12N 9/22; C12N 9/14; C12N 9/16; C12R 1/01
[52] U.S. Cl. ........................... 435/199; 435/195; 435/196; 435/814; 435/815; 435/822; 435/259
[58] Field of Search ............... 435/199, 195, 196, 822, 435/814, 815, 259

[56] References Cited

U.S. PATENT DOCUMENTS

| | | | |
|---|---|---|---|
| 4,064,011 | 12/1977 | Mayer et al. | 435/199 |
| 4,588,689 | 5/1986 | Kado et al. | 435/199 |
| 4,668,631 | 5/1987 | Obayashi et al. | 435/199 |
| 4,693,978 | 9/1987 | Stetter et al. | 435/199 |
| 4,746,609 | 5/1988 | Bolton et al. | 435/199 |

*Primary Examiner*—Amelia Burgess Yarbrough
*Assistant Examiner*—Stephanie W. Zitomer
*Attorney, Agent, or Firm*—Felfe & Lynch

[57] ABSTRACT

The present invention provides a restriction endonuclease which recognizes palindromic sequences

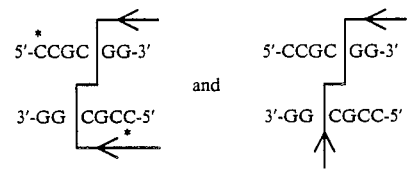

where C* is methylated, and cleaves these sequences at the position indicated by the arrows. This endonuclease is preferably from a microorganism of the genus Kluyvera. The present invention also provides a process for obtaining this new restriction endonuclease and a method for using the endonuclease.

6 Claims, No Drawings

CLASS II RESTRICTION ENDONUCLEASE KSPI AND A PROCESS FOR OBTAINING IT

FIELD OF THE INVENTION

The present invention is concerned with a new Class II restriction endonuclease KspI, with a process for obtaining it and the use thereof.

BACKGROUND AND PRIOR ART

Class II restriction endonucleases are endodeoxyribonucleases, which are able to recognize and cleave certain DNA nucleotide sequences. One phosphodiester bridge is hydrolyzed in each polynucleotide chain of the target sequence. Class II restriction endonucleases are valuable for the analyses of DNA molecules. Specific Class II restriction endonucleases are admittedly already known for numerous recognition sequences. However, their accessibility is often unsatisfactory. In many cases the microorganisms from which the restriction endonucleases are isolated are difficult to cultivate or pathogenic. In addition, the yield is low on large-scale production.

The restriction endonuclease SacII, as described in Gene 47: 1–153 (1986), cleaves DNA at the same position as does the invention. SacII, however, does not cleave DNA sequences containing methylated cytosine at its recognition point. Additionally, SacII is very difficult to separate from related endonuclease SacI, and the yields obtained are very low.

Therefore it is an object of the present invention to provide an isoschizomer for SacII the production of which is simpler and of higher yield and which differentiates between methylated and non methylated DNA sequences.

SUMMARY OF THE INVENTION

Thus according to the present invention, there is provided a restriction endonuclease, which recognizes palindromic DNA sequences:

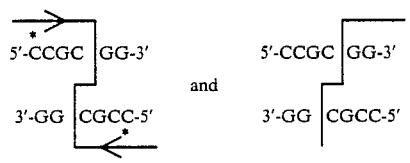

and which cleaves the sequences at the position indicated by the arrows, wherein C* is methylated. The endonuclease may be obtained from a microorganism of genus Kluyvera.

DETAILED DESCRIPTION OF PREFERRED EMBODIMENTS

The new Class II restriction endonuclease according to the present invention, referred to hereafter as KspI, has an average temperature optimum of 37° C. and good activity between pH 7.2 and pH 7.8 in 10 mmol/l Tris/HCl-buffer. Further preferred optimum parameters are 10 mmol/l MgCl$_2$ and 1.0 mmol/l diethioerythritol (DTE). The pH optimum is about 7.5. KspI is an isochizomer for SacII, except that it does not cleave the CCGCGG where the 5' C. is methylated.

The recognition sequence can be ascertained by complete digest of the DNAs of viruses SV40 and adeno 2, the phages λ and ϕX174, the phage derivative M13mp8 and the plasmids pBR322 and pBR328. The DNAs were digested with KspI.

Table 1 shows a comparison between the experimental determined recognition specificity and a computer calculated recognition specificity for an enzyme, which recognizes the sequence CCGCGG.

TABLE 1

| DNA | Number of experimental found cleavage sites | Number of computer-calculated cleavage sites | Experimental found length of fragments | Computer calculated length of fragments | Number of cleavage-sites calculated by computer analysis |
|---|---|---|---|---|---|
| SV40 | 0 | 0 | 0 | 0 | 0 |
| ϕX174 | 1 | 1 | 5400 bp | 5386 bp | at 2862 bp |
| M13mp8 | 0 | 0 | 0 | 0 | 0 |
| pBR322 | 0 | 0 | 0 | 0 | 0 |
| pBR328 | 0 | 0 | 0 | 0 | 0 | bp: base pair(s)

The position of cleavage in the recognition sequence of the enzyme can be ascertained as follows:

DNA of plasmid ϕX174, is linearized with AatII. The 3' end of the AatII fragment is labeled by use of terminal transferase and [α$^{32}$P]-ddATP labeled with $^{32}$P.

After additional digest with AvaII a 2.25 kb fragment which is 3'-labeled at the AatII end is isolated by agarosel gel electrophoresis and is purified from the gel.

Aliquots of this fragment are cleaved with KspI or cleaved base specifically chemically for sequencing (Methods in Enzymology 65: 499–560 (1980). The analysis of the fragments is done by sequence gel electrophoresis (6% polyacrylamide, 8 mol/l urea) and subsequent autoradiography. The interpretation of the results followed Methods in Enzymology 65: 391–401 (1980). It is found that KspI cleaves between position 2862 and 2863 (base pairs) of the sequence of the vector ϕX174 with the specificity as follows:

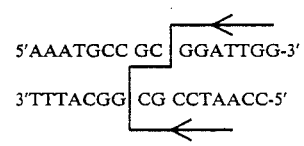

Therefore the endonuclease has specificity:

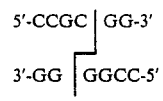

The experimentally found number of cleavage sites is identical with the number of cleavage sites obtained by computer analysis with the different DNAs for the sequence CCGCGG (Table 1). In addition these data were compared with the data from the tables set forth in Gene 10: 357–370 (1980).

According to the present invention KspI is obtained by growing a microorganism of the genus Kluyvera and recovering the enzyme from the cells. In a preferred embodiment of the invention there is used Kluyvera spec DSM 4496. For its recovery, conventional biochemical purification methods can be used wherein the presence of the enzyme can be demonstrated in each of the fragments obtained on the basis of the cleavage pattern of DNA. As substrate λ phage DNA, e.g., can be used. The DNA fragments obtained are separated electrophoretically in agarose gels in the buffer systems conventional for fragment separation in the presence of ethidium bromide.

The microorganism of the genus Kluyvera used for obtaining the enzyme grows anaerobically in Merck Standard I medium.

The microorganism Kluyvera species has been deposited at the "Deutsche Sammlung von Mikroorganismen, Mascheroder Weg 1 b, D-3300 Braunschweig, BRD" and bears accession number DSM 4496. The optimum growth temperature is about 30° C. at pH 7.2–7.8. The cells are doubled after approximately 2 hours of cultivation.

The enzyme is isolated and purified by conventional mechanical and chemical methods, such as high pressure dispersion, ultrasonics or enzymatic digestion.

In a preferred embodiment of the process according to the present invention, the cells are dispersed by a pressure of 5 bar. The cell mass is resuspended in Tris-HCl buffer pH 8.0 which contains protease inhibitors. The cells are dispersed by a French press and precipitated by Streptomycin sulfate and ammonium sulfate. Further purification of the supernatant containing the enzyme is preferably conducted by molecular sieve fractional chromatography, over anion exchangers and over cation exchangers as well as by affinity chromatography. As molecular sieve material, the product which is commercially available under the designation Ultrogel AcA34 (LKB) has proven to be useful.

As anion exchanger the product named DEAE Sephadex Fast Flow (Pharmacia) is useful. As affinity chromatography material heparin-Sepharose CL-6B (Pharmacia) and other chromatography materials are also useful.

The following examples are given for the purpose of illustrating the present invention.

EXAMPLE 1

Kluyvera species DSM 4496 is allowed to grow aerobically at 30° C. for 5 hours and is harvested in the late logarithmic or stationary phase. As medium Merck standard medium I is used. 30 g cell paste is resuspended in 1.5 volumes buffer A (40 mmol/l Tris-Hcl, pH 8.0, 0.1 mmol/l EDTA, 7 mmol/l 2-mercaptoethanol) which contains protease inhibitors. Then the cells are dispersed twice by a French press at 23000 lb/inch². Streptomycin sulfate is added and the precipitate formed is centrifuged and discarded. The supernatant is mixed with 30% to 60% (w/v) ammonium sulphate. The precipitate is isolated and dissolved in 15 ml buffer B (40 mmol/l Tris-HCl pH 8.0, 0.1 mmol/l EDTA, 7 mmol/l 2-mercaptoethanol, 10% (v/v) glycerin). After dialysis against buffer B the solution is fractionated on a heparin Sepharose chromatography column which was equilibrated by buffer B which contains 0.1 mol/l NaCl. For elution a gradient of 0–1.0 mol/l NaCl is used. KspI is found in the fraction between 0.3 and 0.5 mol/l NaCl. The active fractions are precipitated with 80% ammonium sulfate. The precipitate is dissolved in buffer B, dialyzed against buffer B and fractionated on a Ultrogel ACA54 chromatography column which was equilibrated by buffer B which contains 0.5 mmol/l NaCl. The active fractions are dialysed against buffer B and chromatographed on a DEAE-Sepharoze Fast Flow chromatography column which was equilibrated with buffer B. For the elution a gradient of 0–0.5 mol/l NaCl in buffer B is used. KspI is found in the fraction between 0.15 and 0.35 mol/l NaCl.

The active fragments are dialyzed against buffer B and fractionated on a PC11 chromatography column which was equilibrated with 0.2 mol/l NaCl in buffer B. For the elution a gradient of 0.2–1 mol/l NaCl in buffer B is used. KspI is found in the fractions between 0.25 and 0.5 mol/l NaCl.

The active fractions are collected and dialyzed against storage buffer (20 mol/l Tris-HCl pH 8.0, 10 mmol/l 2-mercaptoethanol, 100 mmol/l NaCl, 50% (v/v) glycerin).

EXAMPLE 2

Determination of activity

Definition of the enzyme units: 1 U KspI cleaves 1 μg Lambda-DNA in 1 hour at 37° C. in 25 μl total volume.

Into a mixture of 2.5 μl incubation buffer, containing 80 mmol/l Tris HCl, pH 7.5/37° C., 100 mmol/l magnesium chloride, 500 mmol/l sodium chloride, 100 mmol/l 2-mercaptoethanol and 100 μg/ml BSA (bovine serum albumin) 1.5 μl water and 5 μl Lambda-DNA (optical density: 4 OD/ml) as well as 1 μg KspI-solution (1 U/μl) are added. The solution is maintained at 37° C. for an hour, cooled on ice and mixed with 5 μl cold stop solution, containing 7 mmol/l urea, 20% (w/v) saccharose, 60 mmol/l EDTA and 0.01% (w/v) bromphenol blue. It is then separated electrophoretically on 0.8% agarose gel for 3–4 hours at 100 V. The bands obtained are identified in comparison with suitable DNA length standards.

It will be understood that the specification and examples are illustrative but not limitative of the present invention and that other embodiments within the spirit and scope of the invention will suggest themselves to those skilled in the art.

We claim:

1. A class II restriction endonuclease which recognizes palindromic DNA sequences

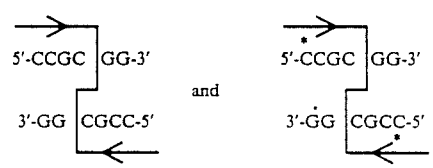

and cleaves said sequences at the positions indicated by the arrows, wherein C* is methylated and said endonuclease is obtained from Kluyvera Spec DSM 4496 microorganisms.

2. The restriction endonuclease of claim 1 wherein said endonuclease is characterized by an average temperature optimum of 37° C. and a pH optimum of between 7.2 and 7.8.

3. A process for obtaining the restriction endonuclease of claim 1 comprising culturing a sample of microorganism Kluyvera spec DSM 4496 under condition of said endonuclease, disrupting said microorganisms and recovering the endonuclease therefrom.

4. The process of claim 3 comprising recovering the endonuclease from said microorganism by dispersing cells of said microorganism to release an extract therefrom, mixing the extract released from the dispersed cells with streptomycin sulfate to form a precipitate and a supernatant separating precipitate from said supernatant, mixing the supernatant with ammonium sulphate in an amount of from 30% to 60% of the saturation point of said supernatant to form a precipitated fraction and recovering the precipitated fraction.

5. The process of claim 4 further comprising purifying the ammonium sulphate precipitated fraction by at least one process selected from the group consisting of molecular sieve fractionation, chromatography over a weakly basic anion exchanger, chromatography over a weakly acidic cation exchanger and affinity chromatography.

6. The process of claim 5 comprising purifying said ammonium sulphate precipitated fraction by affinity chromatography using carrier fixed heparin.

* * * * *

UNITED STATES PATENT AND TRADEMARK OFFICE
CERTIFICATE OF CORRECTION

PATENT NO. : 4,975,376

DATED : December 4, 1990

INVENTOR(S) : Bryan Bolton et al.

It is certified that error appears in the above-identified patent and that said Letters Patent is hereby corrected as shown below:

Column 2, last line change "3'-GCGGCC-5" to -- 3'-GGCGCC-5' --.

Signed and Sealed this

Eighth Day of September, 1992

Attest:

DOUGLAS B. COMER

Attesting Officer     Acting Commissioner of Patents and Trademarks